United States Patent [19]

Kulkarni et al.

[11] Patent Number: 5,066,819

[45] Date of Patent: Nov. 19, 1991

[54] PROCESS FOR THE PREPARATION OF ARYL ESTERS OF N-ALKYL CARBAMIC ACIDS

[75] Inventors: Gurunath H. Kulkarni; Rajan H. Naik; Srinivasachari Rajappa, all of Maharashtra, India

[73] Assignee: Council of Scientific & Industrial Research, New Delhi, India

[21] Appl. No.: 496,427

[22] Filed: Mar. 20, 1990

[51] Int. Cl.$^5$ .................. C07D 317/26; C07D 317/64; C07D 271/44
[52] U.S. Cl. ..................................... 549/438; 549/452; 549/470; 560/132; 560/134; 560/135; 560/136
[58] Field of Search ............... 560/132, 134, 135, 136; 549/438, 452, 470

[56] References Cited

U.S. PATENT DOCUMENTS 4,086,246  4/1978  Toth et al. ........................ 560/132

Primary Examiner—Nicky Chan
Attorney, Agent, or Firm—Ladas & Parry

[57] ABSTRACT

The invention relates to a process for the preparation of aryl esters of N-alkyl carbamic acids. The process comprises reacting an alkyl N-alkyl carbamate of the general formula:

$$R_1\text{—NH—COO—}R_3$$

wherein $R_1$ and $R_3$ are both alkyl groups, with a substituted phenol in the presence of a halogen-containing phosphorous compound to produce an aryl ester of N-alkyl carbamic acid having the general formula:

$$R_1\text{—NH—COO—}R_2$$

wherein $R_1$ is an alkyl group and $R_2$ is an aryl group derived from the substituted phenol. In a preferred embodiment of the invention, the process is used for the preparation of aryl esters of N-methyl carbamic acid.

8 Claims, No Drawings

PROCESS FOR THE PREPARATION OF ARYL ESTERS OF N-ALKYL CARBAMIC ACIDS

The present invention relates to a process for the preparation of aryl esters of N-alkyl carbamic acids. Of particular, but not exclusive, interest to the invention is the preparation of aryl esters of N-methyl carbamic acids.

In essence, the process of the present invention is aimed at the direct conversion of alkyl N-alkyl carbamates to aryl N-alkyl carbamates and this conversion the invention achieves in a facile manner. As far as the applicants are aware, there is no precedent in the prior art for such a conversion which at the best has been shown to be difficult and at the worst impossible. The main reason for this lies in the fact that ester interchange is an equilibrium reaction and such a reaction invariably favours an alkyl ester rather than an aryl ester. Thus, for example, in two recent publications [(S. Hashimoto, I. Furukawa and T. Kuroda, *Tetrahedron Letters*, 1980, 21, 2857) and (J. Barry, S. Bram and A. Petit, *Tetrahedron Letters*, 1988, 29, 4567)], it has been recorded that the attempt to convert a methyl ester into a phenyl ester was totally unsuccessful.

Of the aryl esters of N-alkyl carbamic acids, the aryl esters of N-methyl carbamic acid are particularly sought after in view of their importance as pesticides. Examples of aryl N-methyl carbamates which evince pesticidal activity include 2-sec-butyl-phenyl-N-methyl carbamate, 1-napthyl-N-methyl carbamate, 2,3-dihydro-2,2-dimethyl-7-benzofuranyl N-methyl carbamate, 2-isopropoxyphenyl-N-methyl carbamate and 2-isopropylbenzyl-N-methyl carbamate. These aryl N-methyl carbamates act as cholinesterase inhibitors on contact with insects. Some of them also exhibit nematicidal and miticidal activity.

There are a number of processes described in the prior art specifically directed to the preparation of N-methyl carbamates. For instance, U.S. Pat. Nos. 2,903,478 and 3,009,855 disclose the reaction of a phenol or its sodium salt with phosgene isolation of the phenyl chloroformate and reaction thereof with methylamine.

According to other U.S. Pat. Nos. 3,474,170, 3,474,171, 3,356,690 and 3,111,539, the process disclose involves reacting a phenol or substituted phenol with methyl isocyanate.

More recently, following the Bhopal gas leak tragedy, carbamate production processes have been modified so as to avoid storing the dangerous methyl isocyanate which, immediately after it is generated, is bubbled in to the appropriate phenol to produce phenyl N-methyl carbamate. Examples of such processes are described in European Patent No. 200429 and Indian Patent No. 161739.

It will be clear that all the prior art processes enunciated herein suffer from the fundamental drawback of having to produce in an initial stage the toxic methyl isocyanate. In some instances, phosgene which is also a hazardous substance is employed as a starting material. The involvement of such materials makes it obligatory to take stringent precautions against the accidental leakage of substances such as methyl isocyanate in to the atmosphere. Than again, many of these processes, e.g. that of Indian Patent No. 161739, employ high temperature for pyrolysis and recycling of the reactants.

With the prior art in view, the basic object of the present invention is the provision of a process for the preparation of aryl esters of N-alkyl carbamic acids which substantially reduces the hazards endemic to hitherto known methods.

A more specific object of the invention is the provision of a process for the preparation of aryl esters of N-alkyl carbamic acids which avoids earlier hazards by the direct conversion of alkyl N-alkyl carbamates to aryl N-alkyl carbamates.

Accordingly, the present invention provides a process for the preparation of aryl esters of N-alkyl carbamic acids said esters having the general formula:

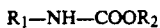

$R_1$—NH—COOR$_2$ wherein $R_1$ is an alkyl group and $R_2$ is an aryl group which comprises reacting an alkyl N-alkyl carbamate of the general formula:

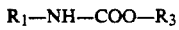

$R_1$—NH—COO—$R_3$ wherein $R_1$ and $R_3$ are both alkyl groups with a substituted phenol in the presence of a halogen-containing phosphorus compound.

Preferably, $R_1$ in either of the above-mentioned formulae is an alkyl group, more specifically methyl. Thus, according to a preferred embodiment, the process of the present invention comprises reacting an alkyl N-alkyl carbamate of the general formula:

$R_1$—NH—COO—$R_3$ wherein $R_1$ is methyl and $R_3$ is methyl or ethyl with a substituted phenol in the presence of a halogen-containing phosphorus compound.

The starting alkyl N-alkyl carbamates employed by the process of the present invention is preferably that prepared by the substantially less hazardous oxidative carbonylation of methylamine process described in co-pending U.S. patent application Ser. No. 07/475747 filed Feb. 6, 1990 and in Indian Patent Application No. 283/Del/89.

The process of the present invention can conveniently be effected at temperatures ranging from 0° C. to 150° C. with or without the presence of a solvent. Where a solvent is employed, this may be selected from solvent such as benzene, toluene, xylene and chlorohydrocarbon solvents.

According to the invention the substituted phenol employed in the reaction is a phenol substituted with from one to three substituent groups equal to or different from one another, said substituent groups being selected from alkyl, alkoxy, alkylthio, alkylamino, alkoxyalkylene, alkylthioalkylene and alkylaminoalkylene groups wherein the alkyl group is a straight or branched group containing from 1 to 5 carbon atoms and the alkylene group contains from one to two carbon atoms; 2,3-dihydro-2,2-dimethyl-benzofuran-7-ol; 2,2-dimethyl-1,3-benzodioxol-4-ol; 2-(1,3-dioxolan-2-yl)-phenol; 1-naphthol or 2-naphthol.

More preferably, the phenol substituent is selected from 2-sec-butylphenyl, 2-isoprpoxyphenyl, 2-isopropylphenyl, 1-naphthyl and 2,3-dihydro-2,2-dimethyl-7-benzofuranyl.

The halogen-containing phosphorus compound employed in the process of the invention is preferably phosphoryl chloride.

At the end of a predetermined time, the reaction is discontinued by quenching the reaction product in water.

The invention will now be illustrated in more detail in the following Examples which should not, however, be construed to limit the scope of the invention in any way.

EXAMPLE 1

1-NAPHTHYL-N-METHYLCARBAMATE

To a solution of 1-naphthyl (1.44 g, 0.01 mole) and ethyl N-methylcarbamate (1.03 g, 0.01 mole) in toluene (15 ml) was added phosphoryl chloride (1.54 g, 0.01 mol) and the mixture was heated at reflux temperature for eight hours. It was poured on to ice cold water and the organic layer separated and washed with cold 5% NaOH solution to remove the unreacted 1-naphthol, followed by water, dried and distilled to give a liquid residue, which solidified on cooling. It was further purified by crystallization, to furnish 1-naphthyl N-methylcarbamate of the formula (IV), m.p. 140°–41° C.; IR: 3305 (NH), 1715 (—COO—), 1600, 1540, 770 (aromatic); PMR (CDCl$_3$, 90 MHz): 2.86 (3H, d, J-7 Hz, NH—CH$_3$), 5.14 (1H, brs, N—H) and 7.17 to 8 (7H, m, aromatic).

EXAMPLE 2

1-NAPHTHYL-N-METHYLCARBAMATE

To a solution of 1-naphthyl (1.44 g, 0.01 mole) and ethyl N-methylcarbamate (1.03 g, 0.01 mole) in dichloroethane (10 ml) was added phosphorus tribromide (2.7 g, 0.01 mol) and the reaction mixture was refluxed for ten hours. It was worked up as described earlier and the crude solid which obtained, was crystallized further to get 1-naphthyl N-methylcarbamate of the formula (IV).

EXAMPLE 3

2-SEC BUTYLPHENYL N-METHYLCARBAMATE

To a solution of 2-sec butylphenol (1.5 g, 0.01 mole) and ethyl N-methylcarbamate (1.03 g, 0.01 mole) in ethylene dichloride (6 ml) was added phosphoryl chloride (0.77 g, 0.05 mole) and the reaction mixture was refluxed under stirring for twenty hours. It was poured onto ice-cold water. The organic layer separated and aqueous layer was extracted with dichloroethane. The combined organic layer was washed with water, dried (Na$_2$SO$_4$) and distilled to give liquid residue, which was further purified by distillation to give 2-sec butyl N-methylcarbamate of the formula (III) [96% by GLC, DV-101 (3%), 150° C., nitrogen, 30 ml/min.] as a liquid, b.p. 110° C. (vap.)/4 mm; IR: 3320 (N—H), 1730 (—COO—), 1535,1490 and 750 (aromatic); PMR (CDCl$_3$, 90 MHz): 0.81 (3H,t, primary methyl of side chain, 1.58 (2H, m, methylene protons of side chain), 2.88 (4H, doublet overlapping a multiplet, NH—CH$_3$ and benzylic proton), 4.97 (1H, br s, N—H) and 6.95 to 7.25 (4H, m, aromatic).

EXAMPLE 4

2-SEC BUTYLPHENYL N-METHYLCARBAMATE

To a solution of 2-sec butylphenol (1.5 g, 0.01 mole) and ethyl N-methylcarbamate (1.03 g, 0.01 mole) in toluene (10 ml) at 60° C., phosphoryl chloride (0.77 g, 0.05 mole) was added dropwise during 0.5 hours and the contents refluxed for 5 hours. It was worked up as described earlier to furnish 2-sec butylphenyl N-methylcarbamate of the formula (III).

EXAMPLE 5

2-SEC BUTYLPHENYL N-METHYLCARBAMATE

To a solution of 2-sec butylphenol (1.5 g, 0.01 mole) and ethyl N-methylcarbamate (1.03 g, 0.01 mole) was added phosphorus tribromide (2.7 g, 0.01 mole) and the contents were heated at 140° C. for 15 hours. The reaction mixture was worked up as described earlier to give 2-sec butylphenyl N-methylcarbamate, identified by spectral data.

EXAMPLE 6

2-SEC BUTYLPHENYL N-METHYLCARBAMATE

To a solution of 2-sec butylphenol (1.5 g, 0.01 mole) and ethyl N-methylcarbamate (1.03 g, 0.01 mole), along with phosphorus pentachloride (1.05 g, 0.05 mole) in toluene (10 ml) was stirred at 28° C. and afterwards it was refluxed for 7 hours and worked up as usual to get the title compound.

EXAMPLE 7

2-SEC BUTYLPHENYL N-METHYLCARBAMATE

To a stirred and ice cold solution of ethyl N-methylcarbamate (1.03 g, 0.01 mole) and phosphorus tribromide (2.7 g, 0.01 mole) in dichloroethane (10 ml) was added a solution of 2-sec butylphenol (1.5 g, 0.01 mole) in dichloroethane (5 ml) dropwise during 15 min. and the mixture was stirred at 5° C. to 10° C. for two hours. It was then refluxed for four hours worked up as described earlier to give compound of the formula (III).

EXAMPLE 8

2-ISOPROPOXYPHENYL N-METHYLCARBAMATE

To a solution of 2-isopropoxyphenol (1.52 g, 0.01 mole) and ethyl N-methylcarbamate (1.03 g,,0.01 mole) in dichloroethane (10 ml, was added phosphoryl chloride (1.54 g, 0.01 mole) and refluxed for six hours. The reaction mixture was worked up as described earlier to give 2-isopropoxyphenyl N-methylcarbamate of the formula (VI) as a solid, crystallised from pet. ether, m.p. 89° C. to 90° C.

EXAMPLE 9

2-ISOPROPOXYPHENYL N-METHYLCARBAMATE

To a solution of 2-isopropoxyphenol (1.38 g, 0.01 mole) and ethyl N-methylcarbamate (1.03 g, 0.01 mole) in toluene (10 ml), was added phosphoryl chloride (1.54 g, 0.01 mole) and refluxed for six hours. The reaction mixture was worked up as described earlier to give 2-isopropylphenyl N-methylcarbamate of the formula (VII) as a solid, crystallised from pet. ether, m.p. 88° C. to 93° C.

EXAMPLE 10

2-SEC BUTYLPHENYL N-METHYLCARBAMATE

To a mixture of methyl N-methylcarbamate (0.89 g, 0.01 mole) and 2-sec butylphenol (1.5 g, 0.01 mole) in dichloroethane (10 ml), a solution of phosphorus tribromide (2.7 g, 0.01 mole) in dichloro-ethane (6 ml) was added and the mixture was refluxed for eight hours. It was then worked up and purified as described earlier to give 2-sec butylphenyl N-methylcarbamate of the formula (III).

The process of the present invention represents the great improvement over the prior art. From what was known hitherto, it was not obvious that the facile conversion of alkyl N-alkyl carbamate esters to aryl N-alkyl carbamate esters could have been predicted. The present invention embodies this novel concept of achieving the conversion through an irreversible reaction.

We claim:

1. A process for the preparation of aryl esters of N-alkyl carbamic acids, said esters having the general formula:

$$R_1-NH-COOR_2$$

wherein $R_1$ is an alkyl group and $R_2$ is an aryl group which comprises reacting an alkyl N-alkyl carbamate of the general formula:

$$R_1-NH-COO-R_3$$

wherein $R_1$ and $R_3$ are both alkyl groups, with a substituted phenol in the presence of a halogen-containing of phosphorous compound selected from the group consisting of phosphoryl chloride, phosphorous tribromide and phosphorus pentachloride, the $R_2$ aryl group being derived from the substituted phenol reactant.

2. A process as claimed in claim 1 wherein $R_1$ is methyl or ethyl, said alkyl N-alkyl carbamate being correspondingly either methyl N-methyl carbamate or ethyl N-methyl carbamate.

3. A process as claimed in claim 1 wherein said substituted phenol is phenol substituted with from one to three substituent groups equal to or different from one another, said substituent groups being selected from alkyl, alkoxy, alkylthio, alkylamino, alkoxyalkylene, alkylthioalkylene and alkylaminoalkylene groups wherein the alkyl group is a straight or branched group containing from 1 to 5 carbon atoms and the alkylene group contains from one to two carbon atoms; 2,3-dihydro-2,2-dimethylbenzofuran-7-ol; 2,2-dimethyl-1,3-benzo-dioxol-4-ol; 2-(1,3-dioxolan-2-yl)-phenol; 1-naphthol or 2-naphthol.

4. A process as claimed in claim 1 wherein the $R_2$ aryl group is selected from 2-sec-butylphenyl, 2-isoprpoxyphenyl, 2-isopropylphenyl, 1-naphthyl and 2,3-dihydro-2,2-dimethyl-7-benzofuranyl.

5. A process as claimed in claim 1 wherein the halogen-containing phosphorus compound is phosphoryl chloride.

6. A process as claimed in claim 1 wherein said reaction is effected at a temperature in the range of from 0° C. to 150° C.

7. A process as claimed in claim 1 wherein the reaction is effected in the presence of a solvent selected from the group consisting of benzene, toluene, xylene and chlorohydrocarbon solvents.

8. A process as claimed in claim 1 wherein the reaction is discontinued by quenching the reaction product in water.

* * * * *